United States Patent
Nelson et al.

(10) Patent No.: US 9,286,438 B2
(45) Date of Patent: Mar. 15, 2016

(54) SYSTEMS AND METHODS FOR PRODUCING CHEMICAL ARRAY LAYOUTS

(75) Inventors: Charles F. Nelson, San Carlos, CA (US); Amitabh Shukla, San Jose, CA (US); Jing Gao, Santa Clara, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 1306 days.

(21) Appl. No.: 12/826,500

(22) Filed: Jun. 29, 2010

(65) Prior Publication Data

US 2010/0267588 A1 Oct. 21, 2010

Related U.S. Application Data

(63) Continuation of application No. 11/349,425, filed on Feb. 6, 2006, now abandoned.

(60) Provisional application No. 60/751,777, filed on Dec. 15, 2005.

(51) Int. Cl.
*G06F 19/10* (2011.01)
*G06F 19/20* (2011.01)

(52) U.S. Cl.
CPC .................................... *G06F 19/20* (2013.01)

(58) Field of Classification Search
None
See application file for complete search history.

(56) References Cited

U.S. PATENT DOCUMENTS

| | | | |
|---|---|---|---|
| 6,456,955 | B1 | 9/2002 | Andrews et al. |
| 6,804,679 | B2 | 10/2004 | Jevons et al. |
| 2002/0183936 | A1 | 12/2002 | Kulp et al. |
| 2003/0097222 | A1 | 5/2003 | Craford et al. |
| 2003/0120432 | A1 | 6/2003 | Zhou et al. |
| 2004/0049354 | A1 | 3/2004 | Loraine et al. |
| 2004/0142371 | A1 | 7/2004 | Milosavljevic et al. |

OTHER PUBLICATIONS

Webb et al. "Systems and Methods for Producing Chemical Arrays Layout," U.S. Appl. No. 11/000,681, filed Nov. 30, 2004, 60 pages.
Webb et al. "Systems and Methods for Producing Chemical Arrays Layout," U.S. Appl. No. 11/001,672, filed Nov. 30, 2004, 87 pages.
Webb et al. "Systems and Methods for Producing Chemical Arrays Layout," U.S. Appl. No. 11/001,700, filed Nov. 30, 2004, 74 pages.

*Primary Examiner* — Lori A Clow

(57) ABSTRACT

Systems and methods for using the same to obtain a chemical array layout are provided. Also provided are computer program products for executing the subject methods.

20 Claims, 5 Drawing Sheets

SYSTEMS AND METHODS FOR PRODUCING CHEMICAL ARRAY LAYOUTS

CROSS-REFERENCE TO RELATED APPLICATION

This application is a Continuation application of U.S. Ser. No. 11/349,425, filed on Feb. 6, 2006, entitled "SYSTEMS AND METHODS FOR PRODUCING CHEMICAL ARRAY LAYOUTS," which claims priority pursuant to 35 U.S.C. §119 (e) of U.S. Ser. No. 60/751,777 filed on Dec. 15, 2005; the disclosures of which are herein incorporated by reference.

BACKGROUND

Arrays of chemical binding agents, such as nucleic acids and polypeptides, have become an increasingly important tool in the biotechnology industry and related fields. These chemical (i.e., binding agent or ligand) arrays, in which a plurality of chemical binding agents are positioned on a solid support surface in the form of an array or pattern, find use in a variety of applications, including gene expression analysis, drug screening, nucleic acid sequencing, mutation analysis, comparative genome hybridization, location analysis and the like.

SUMMARY OF THE INVENTION

Systems and methods for using the same to obtain a chemical array layout are provided.

Aspects of the invention include a system for producing an array layout, where the system includes an input manager for receiving array request information from a user. The system further includes a processing module that includes both an array set developer and an array layout developer. In certain embodiments, the array set developer is configured to: identify a total number of features required to array display a selected portion of the probe content of array request information, where the selected portion may be the entire probe content or a fraction thereof; and evaluate whether the identified total number of features exceeds a single array format feature number limit to determine whether a single array format or an array set of two or more array formats is required to array display said total number of features to provide an array set decision. The processing module of these embodiments also includes an array layout developer having a memory that includes a plurality of rules relating to array layout design, wherein the array layout developer is configured to develop an array layout for a single array format or an array set of two or more array formats based on the application of one or more of the rules to information that includes both array request information received from a user and an array set decision. The systems may also include an output manager for providing a first version of an array layout to a user.

In certain embodiments, the array developer communicates the array set decision to a user for acceptance prior to providing the array set decision to said array layout developer. In certain embodiments, the array set decision is that a single array format can array display the total number of array features and the array layout developer develops an array layout for a single array format. In certain embodiments the array set decision is that an array set of two or more array formats is required to array display the total number of array features, and the array layout developer develops an array set layout. In certain embodiments, at least a portion of the probe content of the total number of features is distributed among the features of the array set layout in a random fashion. In certain embodiments, at least a portion of the probe content of the total number of features is distributed among the features of the array set layout in a non-random fashion. In certain embodiments, the array set layout includes at least one probe group, such as a control probe group or an experimental probe group, of features that is present in each array format of the array set.

In certain embodiments, the system includes a memory that stores a plurality of versions of an array layout. In certain embodiments, at least two of the versions are generated in response to input from a single user, while in other embodiments at least two of the versions are generated in response to input from at least two users. In certain embodiments, the processing module further includes a differencing engine for comparing the at least two versions.

In certain embodiments, the output manager communicates with an interface which displays differences between compared versions. In certain embodiments, a second version may be modified by a user to include a characteristic of the first version. In certain embodiments, a new version of the array layout is generated which incorporates the modification. In certain embodiments, a second version may be modified by a user to eliminate a characteristic of the second version not present in the first version. In certain embodiments, a new version of the array layout is generated which incorporates the modification.

In certain embodiments, the rules are modifiable by a permitted user of the system. In certain embodiments, the array layout includes the organization of probe content on the array. In certain embodiments, the array format includes system-defined layout parameters selected from the group consisting of numbers of features, density of features, dimensions of features, shape of features, size of interfeature areas, size of inter-array areas, organization of probe content. In certain embodiments, the system-defined parameters include user-defined layout parameters.

In certain embodiments, the system further includes one or more of the following:

(i) an array customizing manager configured to allow an array layout developer to develop an array that includes a first set of probe sequences provided by a user and a second set of probe sequences provided by an additional party;

(ii) an array request information manager to provide a history of array request information to a user;

(iii) an array layout format manager configured to provide an array layout format based on array request information;

(iv) an array layout customizing manager configured to receive a customer input array layout and suggest an alternative layout developed from information not provided by a user;

(v) an array layout comparison manager configured to compare an array layout to a database of one or more array layouts; and (vi) a default probe set selection manager that allows a user to include or exclude a predetermined set of probes in an array layout.

In certain embodiments, the system includes a communication module that provides for remote communication between a user and said processor module. In certain embodiments, the communication module provides for communication between a user and a chemical processor module via the Internet. In certain embodiments, the communication module provides for a graphical user interface (GUI) between a user and a processing module.

Aspects of the invention further include methods of obtaining an array layout for a chemical array, where the methods may include inputting array request information into a system according to an embodiment of the invention; and obtaining an array layout from the system. The inputting may be via the Internet. The inputting may be via a graphical user interface. In certain embodiments, the methods further include ordering one or more chemical arrays having an array layout via produced by the system from a chemical array vendor. In certain embodiments, the method further comprises receiving the one or more ordered chemical arrays from the chemical array vendor.

Aspects of the invention further include methods of producing an array layout for a chemical array, where embodiments of the methods include receiving from a user array request information into a system according to an embodiment of the invention; and obtaining an array layout from said system to produce said array layout. The receiving may be via the Internet. The receiving may be via a graphical user interface. In certain embodiments, the method further includes producing one or more chemical arrays having the array layout. In certain embodiments, the method further includes shipping the one or more chemical arrays to a customer.

Aspects of the invention further includes a computer program product that includes a computer readable storage medium having a computer program stored thereon, wherein the computer program, when loaded onto a computer, operates the computer to: receive chemical array request information from a user; develop an array layout based on the received information and an array set decision by applying one or more array layout design rules to the received information and array set decision; and provide the array layout to a user.

BRIEF DESCRIPTIONS OF THE DRAWINGS

Figure 4:
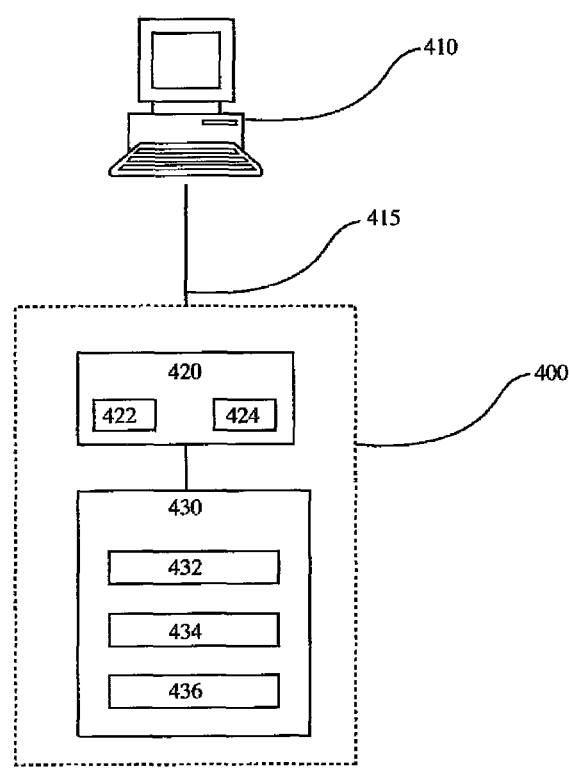
Figure 5:
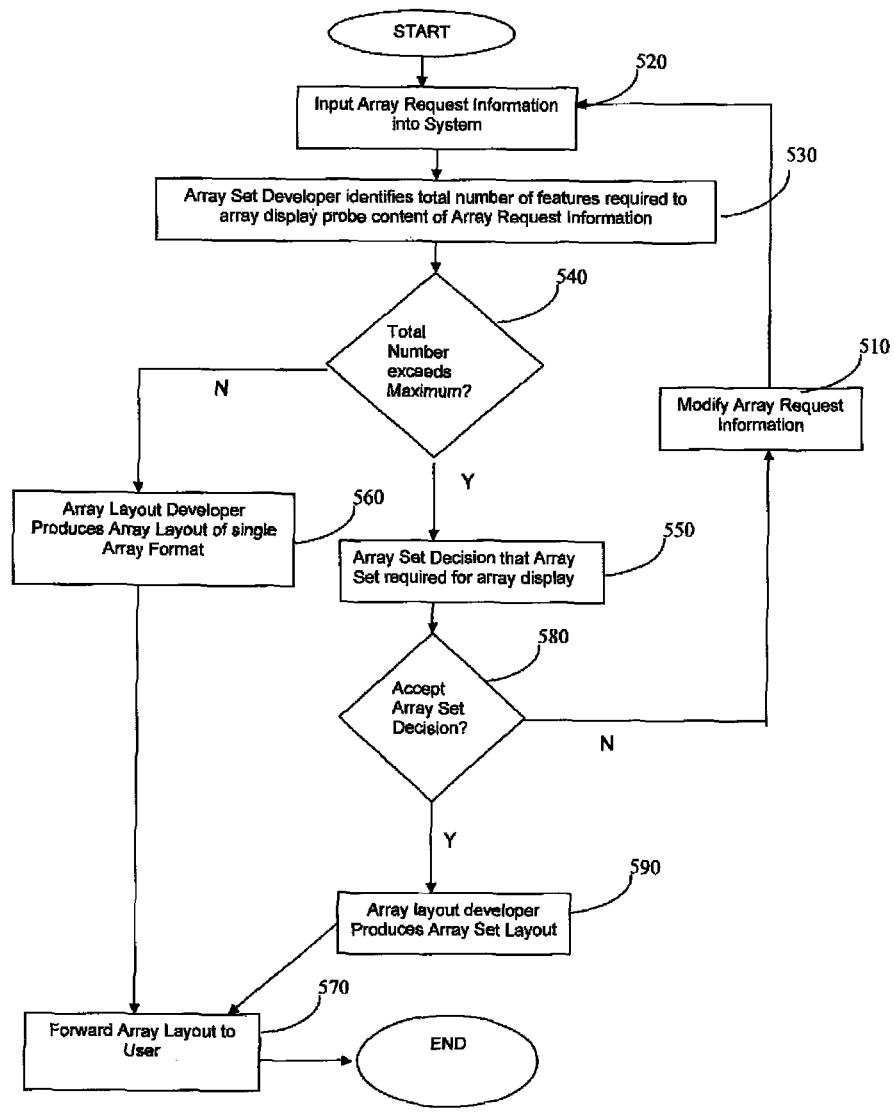
Figure 6:
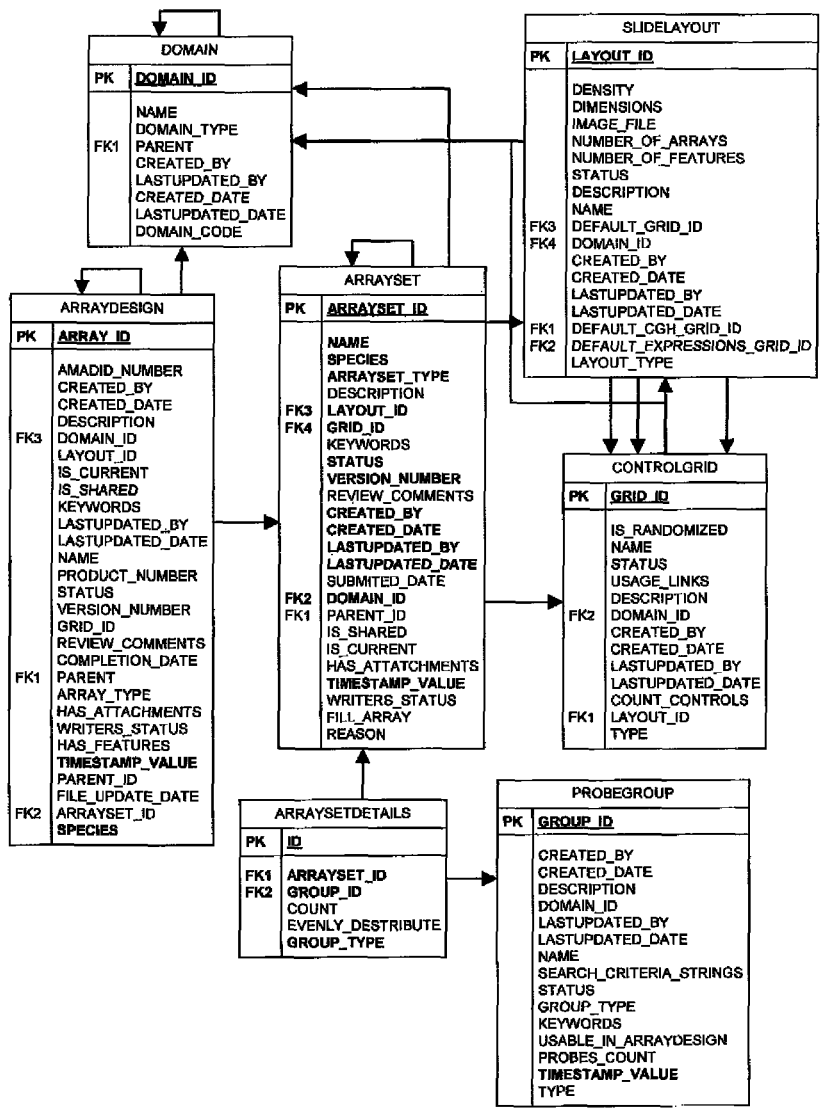
Figure 7:
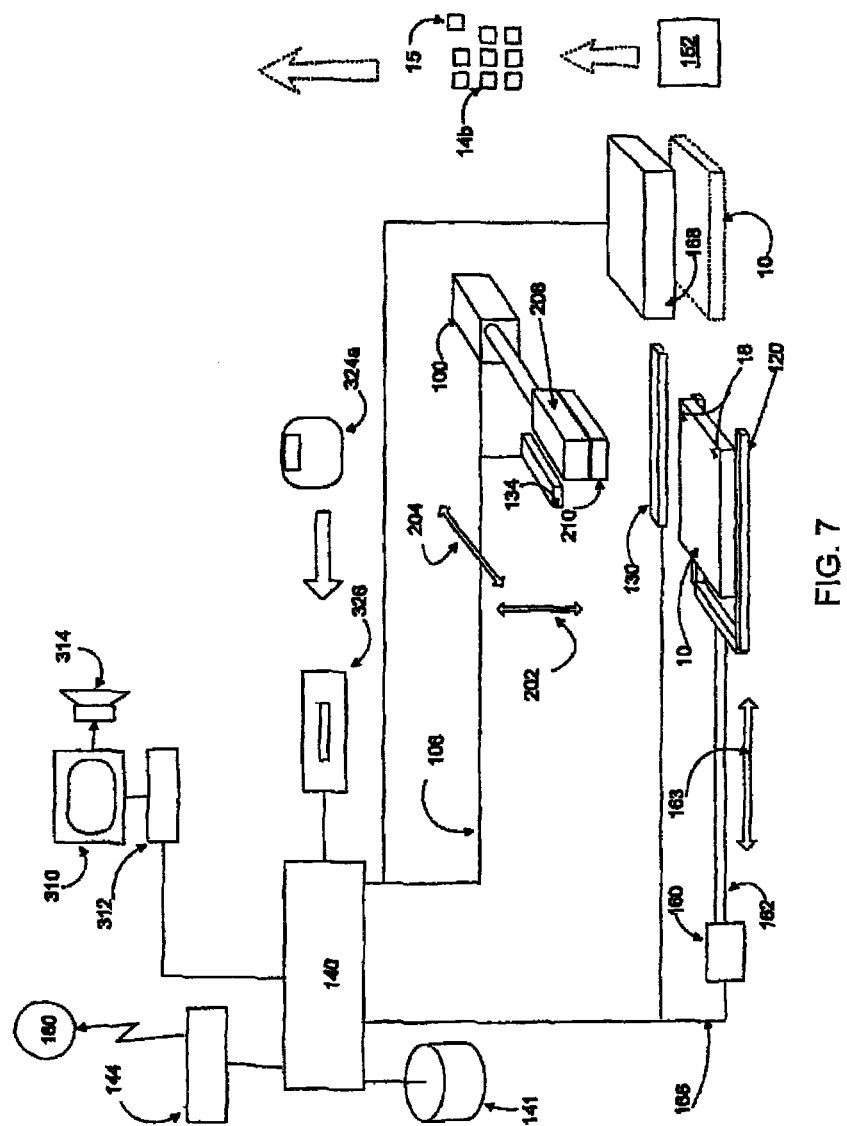

FIG. 4 schematically illustrates some methods and apparatus of the present invention;

FIG. 5 depicts a block diagram showing the interaction of an array set developer and array layout developer in producing an array layout according to an embodiment of the present invention;

FIG. 6 provides a block diagram showing the interrelationships of different domains of a representative system according to an embodiment of the invention;

FIG. 7 is a schematic diagram illustrating a fabrication station of the present invention.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

By "array layout" is meant a collection of information, e.g., in the form of a file, which represents the location of probes that have been assigned to specific features of one or more array formats, e.g., a single array format or two or more array formats of an array set.

The phrase "array format" refers to a format that defines an array by feature number, feature size, cartesian coordinates of each feature, and distance that exists between features within a given single array.

The phrase "single array format feature number limit" refers to the upper limit of the feature number that can be present in a given single array.

The phrase "array set" refers to a collection of probe content in which the number of features required for display of the collection exceeds a single array format feature number limit, such that the array set is made up of sufficient probe content to populate more than a single array format, e.g., 2 or more array formats, 3 or more array formats, 4 or more array formats, 5 or more array formats, etc.

By "array set layout" is meant a collection of information, e.g., in the form of a file, which represents the location of probes making up the collection of probe content of an array set that have been assigned to specific features of an array format of an array set. An array set layout is an array layout that encompasses an array set of two or more array formats.

An "array set decision" is a decision made by an array set developer module that determines whether the total number of features required to array display a desired portion of the probe content of an array request information can be present in a single array format or exceeds an array format feature number limit such that an array set of two or more array formats is required for array display of the desired portion of the probe content of the array request information.

To "array display" means to produce a probe feature on a substrate surface. As such, probe content is array displayed when features are produced on an array substrate that include the probes of the probe content.

The phrase "array request information" is use broadly to encompass any type of information/data that is employed in developing an array layout, where representative types of array request information include, but are not limited to: probe content identifiers, e.g., in the form of probe sequence, gene name, accession number, annotation, etc.; array function information, e.g., in the form of types of genes to be studied using the array, such as genes from a specific species (e.g., mouse, human), genes associated with specific tissues (e.g., liver, brain, cardiac), genes associated with specific physiological functions, (e.g., apoptosis, stress response), genes associated with disease states (e.g., cancer, cardiovascular disease), etc.; array format information, e.g., feature number, feature size, cartesian coordinates of each feature, and distance that exists between features within a given array; etc.

A "data element" represents a property of a probe sequence, which can include the base composition of the probe sequence. Data elements can also include representations of other properties of probe sequences, such as expression levels in one or more tissues, interactions between a sequence (and/or its encoded products), and other molecules, a representation of copy number, a representation of the relationship between its activity (or lack thereof) in a cellular pathway (e.g., a signaling pathway) and a physiological response, sequence similarity to other probe sequences, a representation of its function, a representation of its modified, processed, and/or variant forms, a representation of splice variants, the locations of introns and exons, functional domains etc. A data element can be represented for example, by an alphanumeric string (e.g., representing bases), by a number, by "plus" and "minus" symbols or other symbols, by a color hue, by a word, or by another form (descriptive or nondescriptive) suitable for computation, analysis and/or processing for example, by a computer or other machine or system capable of data integration and analysis.

As used herein, the term "data structure" is intended to mean an organization of information, such as a physical or logical relationship among data elements, designed to support specific data manipulation functions, such as an algorithm. The term can include, for example, a list or other collection type of data elements that can be added, subtracted, combined or otherwise manipulated. Exemplarily, types of data structures include a list, linked-list, doubly linked-list, indexed list, table, matrix, queue, stack, heap, dictionary, flat file databases, relational databases, local databases, distributed databases, thin client databases and tree. The term also can include organizational structures of information that relate or correlate, for example, data elements from a plurality of data structures or other forms of data management structures. A specific example of information organized by a data structure of the invention is the association of a plurality of data elements relating to a gene, e.g., its sequence, expression level in one or more tissues, copy number, activity states (e.g., active or non-active in one or more tissues), its modified, processed and/or and/or variant forms, splice variants encoded by the gene, the locations of introns and exons, functional domains, interactions with other molecules, function, sequence similarity to other probe sequences, etc. A data structure can be a recorded form of information (such as a list) or can contain additional information (e.g., annotations) regarding the information contained therein. A data structure can include pointers or links to resources external to the data structure (e.g., such as external databases). In one aspect, a data structure is embodied in a tangible form, e.g. is stored or represented in a tangible medium (such as a computer readable medium).

The term "object" refers to a unique concrete instance of an abstract data type, a class (that is, a conceptual structure including both data and the methods to access it) whose identity is separate from that of other objects, although it can "communicate" with them via messages. In some occasions, some objects can be conceived of as a subprogram which can communicate with others by receiving or giving instructions based on its, or the others' data or methods. Data can consist of numbers, literal strings, variables, references, etc. In addition to data, an object can include methods for manipulating data. In certain instances, an object may be viewed as a region of storage. In the present invention, an object typically includes a plurality of data elements and methods for manipulating such data elements.

A "relation" or "relationship" is an interaction between multiple data elements and/or data structures and/or objects. A list of properties may be attached to a relation. Such properties may include name, type, location, etc. A relation may be expressed as a link in a network diagram. Each data element may play a specific "role" in a relation.

As used herein, an "annotation" is a comment, explanation, note, link, or metadata about a data element, data structure or object, or a collection thereof. Annotations may include pointers to external objects or external data. An annotation may optionally include information about an author who created or modified the annotation, as well as information about when that creation or modification occurred. In one embodiment, a memory comprising a plurality of data structures organized by annotation category provides a database through which information from multiple databases, public or private, may be accessed, assembled, and processed. Annotation tools include, but are not limited to, software such as BioFerret (available from Agilent Technologies, Inc., Palo Alto, Calif.), which is described in detail in application Ser. No. 10/033,823 filed Dec. 19, 2001 and titled "Domain-Specific Knowledge-Based Metasearch System and Methods of Using." Such tools may be used to generate a list of associations between genes from scientific literature and patent publications.

As used herein an "annotation category" is a human readable string to annotate the logical type the object comprising its plurality of data elements represents. Data structures that contain the same types and instances of data elements may be assigned identical annotations, while data structures that contain different types and instances of data elements may be assigned different annotations.

As used herein, a "probe sequence identifier" or an "identifier corresponding to a probe sequence" refers to a string of one or more characters (e.g., alphanumeric characters), symbols, images or other graphical representation(s) associated with a probe sequence comprising a probe sequence such that the identifier provides a "shorthand" designation for the sequence. In one aspect, an identifier comprises an accession number or a clone number. An identifier may comprise descriptive information. For example, an identifier may include a reference citation or a portion thereof.

As used herein "probe request information" refers to any type of information that is employed to obtain one or more probes, and may comprise one or more search terms, key words, accession numbers, or probe sequences. Probe request information may take a number of different forms, such as sequence information, location identifier information, art accepted identifier, e.g., accession no, information, etc. Likewise, probe content information may take a number of different forms, such as sequence information, location identifier information, art accepted identifier, e.g., accession no, information, etc. In one aspect, "probe content information" includes a probe sequence or an identifier associated therewith, structural, and functional genomic and/or proteomic information with respect to the probe sequence and/or identifier. In another aspect, probe content information is relevant links to reagents or kits that might be used to obtain additional probe content information (e.g., such as links to sources of primers, antibodies, binding partners, and host cells, including transgenic animals expressing the sequences or modified forms there of, and the like). In other aspects, probe content information may include, but is not limited to information regarding cell(s) or tissue(s) in which a probe sequence is expressed and/or levels of expression, information concerning physiological responses of a cell or tissue in which the sequence is expressed (e.g., whether the cell or tissue is from a patient with a disease), chromosomal location information, copy number information, information relating to similar sequences (e.g., homologous, paralogous or orthologous sequences). Additional probe content information can include frequency of the sequence in a population, information relating to polymorphic variants of the probe sequence (e.g., such as SNPs), information relating to splice variants (e.g., tissues, individuals in which such variants are expressed), and or demographic information relating to individual(s) in which the sequence is found.

The phrase "best-fit" refers to a resource allocation scheme that determines the best result in response to input data. The definition of 'best' may vary depending on a given set of predetermined parameters, such as sequence identity limits, signal intensity limits, cross-hybridization limits, Tm, base composition limits, probe length limits, distribution of bases along the length of the probe, distribution of nucleation points along the length of the probe (e.g., regions of the probe likely to participate in hybridization, secondary structure parameters, etc. In one aspect, the system considers predefined thresholds. In another aspect, the system rank-orders fit. In a further aspect, the user defines his or her own thresholds, which may or may not include system-defined threshold.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that many computer-based systems are available which are suitable for use in the present invention. The data storage means may comprise any manufacture comprising a recording of the present information as described above, or a memory access means that can access such a manufacture.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

"Computer readable medium" as used herein refers to any storage or transmission medium that participates in providing instructions and/or data to a computer for execution and/or processing. Examples of storage media include floppy disks, magnetic tape, UBS, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. A file may be stored in permanent memory.

With respect to computer readable media, "permanent memory" refers to memory that is permanently stored on a data storage medium. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "memory" or "memory unit" refers to any device which can store information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

Items of data are "linked" to one another in a memory when the same data input (for example, filename or directory name or search term) retrieves the linked items (in a same file or not) or an input of one or more of the linked items retrieves one or more of the others.

The term "monomer" as used herein refers to a chemical entity that can be covalently linked to one or more other such entities to form a polymer. Of particular interest to the present application are nucleotide "monomers" that have first and second sites (e.g., 5' and 3' sites) suitable for binding to other like monomers by means of standard chemical reactions (e.g., nucleophilic substitution), and a diverse element which distinguishes a particular monomer from a different monomer of the same type (e.g., a nucleotide base, etc.). In the art synthesis of nucleic acids of this type utilizes an initial substrate-bound monomer that is generally used as a building-block in a multi-step synthesis procedure to form a complete nucleic acid. A "biomonomer" references a single unit, which can be linked with the same or other biomonomers to form a biopolymer (e.g., a single amino acid or nucleotide with two linking groups, one or both of which may have removable protecting groups).

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "amino acid" is intended to include not only the L, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, $\epsilon$-nicotinoyl-lysine, isonipecotic acid, tetrahydroisoquinoleic acid, $\alpha$-aminoisobutyric acid, sarcosine, citrulline, cysteic acid, t-butylglycine, t-butylalanine, phenylglycine, cyclohexylalanine, $\beta$-alanine, 4-aminobutyric acid, and the like.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure. In the practice of the instant invention, oligomers will generally comprise about 2-50 monomers, preferably about 2-20, more preferably about 3-10 monomers.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

A "biopolymer" is a polymer of one or more types of repeating units. Biopolymers are typically found in biological systems (although they may be made synthetically) and may include peptides or polynucleotides, as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. For example, a "biopolymer" may include DNA (including cDNA), RNA, oligonucleotides, and PNA and other polynucleotides as described in U.S. Pat. No. 5,948,902 and references cited therein (all of which are incorporated herein by reference), regardless of the source.

The term "biomolecule" means any organic or biochemical molecule, group or species of interest that may be formed in an array on a substrate surface. Exemplary biomolecules include peptides, proteins, amino acids and nucleic acids.

The term "ligand" as used herein refers to a moiety that is capable of covalently or otherwise chemically binding a compound of interest. The arrays of solid-supported ligands produced by the methods can be used in screening or separation processes, or the like, to bind a component of interest in a sample. The term "ligand" in the context of the invention may or may not be an "oligomer" as defined above. However, the term "ligand" as used herein may also refer to a compound that is "pre-synthesized" or obtained commercially, and then attached to the substrate.

The term "sample" as used herein relates to a material or mixture of materials, typically, although not necessarily, in fluid form, containing one or more components of interest.

A biomonomer fluid or biopolymer fluid reference a liquid containing either a biomonomer or biopolymer, respectively (typically in solution).

The term "peptide" as used herein refers to any polymer compound produced by amide formation between an α-carboxyl group of one amino acid and an α-amino group of another group.

The term "oligopeptide" as used herein refers to peptides with fewer than about 10 to 20 residues, i.e., amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single-stranded nucleotide multimers of from about 10 up to about 200 nucleotides in length, e.g., from about 25 to about 200 nt, including from about 50 to about 175 nt, e.g. 150 nt in length The term "polynucleotide" as used herein refers to single- or double-stranded polymers composed of nucleotide monomers of generally greater than about 100 nucleotides in length.

An "array," or "chemical array' used interchangeably includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. As such, an addressable array includes any one or two or even three-dimensional arrangement of discrete regions (or "features") bearing particular biopolymer moieties (for example, different polynucleotide sequences) associated with that region and positioned at particular predetermined locations on the substrate (each such location being an "address"). These regions may or may not be separated by intervening spaces. In the broadest sense, the arrays of many embodiments are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays may be fabricated using drop deposition from pulse jets of either precursor units (such as nucleotide or amino acid monomers) in the case of in situ fabrication, or the previously obtained biomolecule, e.g., polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. Other drop deposition methods can be used for fabrication, as previously described herein.

Figure 1:
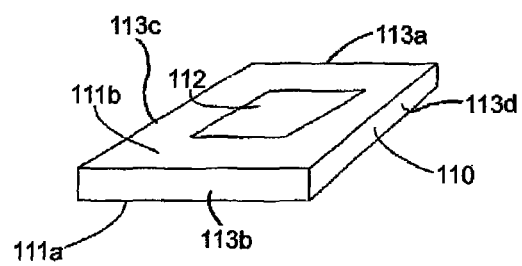
FIG. 1 illustrates a substrate carrying multiple arrays, such as may be fabricated by methods of the present invention.
Figure 2:
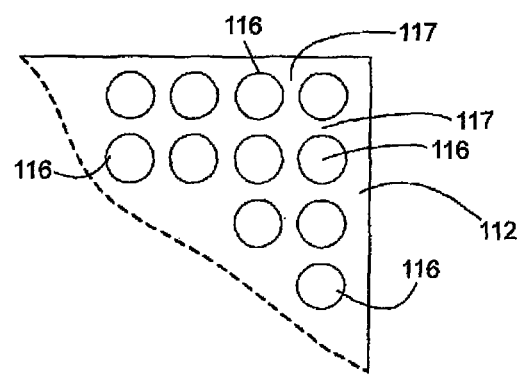
FIG. 2 is an enlarged view of a portion of FIG. 1 showing multiple ideal spots or features.
Figure 3:
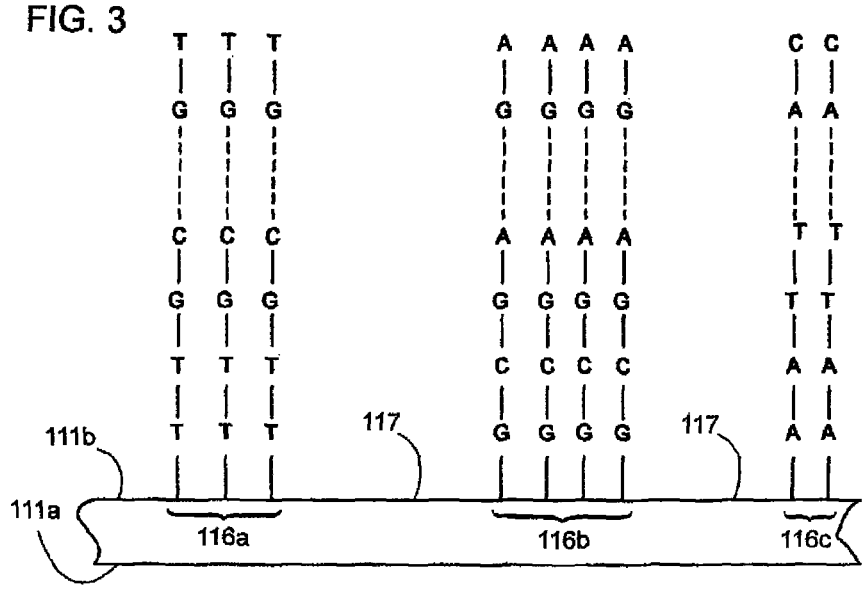
FIG. 3 is an enlarged illustration of a portion of the substrate in FIG. 2.

An exemplary chemical array is shown in FIGS. 1-3, where the array shown in this representative embodiment includes a contiguous planar substrate 110 carrying an array 112 disposed on a surface 111b of substrate 110. It will be appreciated though, that more than one array (any of which are the same or different) may be present on surface 111b, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the surface 111b, with regions of the rear surface 111b adjacent the opposed sides 113c, 113d and leading end 113a and trailing end 113b of slide 110, not being covered by any array 112. A second surface 111a of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of biopolymer ligands, e.g., in the form of polynucleotides. As mentioned above, all of the features 116 may be different, or some or all could be the same. The interfeature areas 117 could be of various sizes and configurations. Each feature carries a predetermined biopolymer such as a predetermined polynucleotide (which includes the possibility of mixtures of polynucleotides). It will be understood that there may be a linker molecule (not shown) of any known types between the rear surface 111b and the first nucleotide.

Substrate 110 may carry on surface 111a, an identification code, e.g., in the form of bar code (not shown) or the like printed on a substrate in the form of a paper label attached by adhesive or any convenient means. The identification code contains information relating to array 112, where such information may include, but is not limited to, an identification of array 112, i.e., layout information relating to the array(s), etc.

The substrate may be porous or non-porous. The substrate may have a planar or non-planar surface.

In those embodiments where an array includes two more features immobilized on the same surface of a solid support, the array may be referred to as addressable. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

An array "assembly" includes a substrate and at least one chemical array, e.g., on a surface thereof. Array assemblies may include one or more chemical arrays present on a surface of a device that includes a pedestal supporting a plurality of prongs, e.g., one or more chemical arrays present on a surface of one or more prongs of such a device. An assembly may include other features (such as a housing with a chamber from which the substrate sections can be removed). "Array unit" may be used interchangeably with "array assembly".

"Hybridizing" and "binding", with respect to polynucleotides, are used interchangeably.

The term "substrate" as used herein refers to a surface upon which marker molecules or probes, e.g., an array, may be adhered. Glass slides are the most common substrate for biochips, although fused silica, silicon, plastic and other materials are also suitable.

When two items are "associated" with one another they are provided in such a way that it is apparent one is related to the other such as where one references the other. For example, an array identifier can be associated with an array by being on the array assembly (such as on the substrate or a housing) that carries the array or on or in a package or kit carrying the array assembly. "Stably attached" or "stably associated with" means an item's position remains substantially constant where in certain embodiments it may mean that an item's position remains substantially constant and known.

A "web" references a long continuous piece of substrate material having a length greater than a width. For example, the web length to width ratio may be at least 5/1, 10/1, 50/1, 100/1, 200/1, or 500/1, or even at least 1000/1.

"Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C.

"Rigid" refers to a material or structure which is not flexible, and is constructed such that a segment about 2.5 by 7.5 cm retains its shape and cannot be bent along any direction more than 60 degrees (and often not more than 40, 20, 10, or 5 degrees) without breaking.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

"Contacting" means to bring or put together. As such, a first item is contacted with a second item when the two items are brought or put together, e.g., by touching them to each other.

"Depositing" means to position, place an item at a location—or otherwise cause an item to be so positioned or placed at a location. Depositing includes contacting one item with another. Depositing may be manual or automatic, e.g., "depositing" an item at a location may be accomplished by automated robotic devices.

By "remote location," it is meant a location other than the location at which the array (or referenced item) is present and hybridization occurs (in the case of hybridization reactions). For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart.

"Communicating" information means transmitting the data representing that information as signals (e.g., electrical, optical, radio signals, and the like) over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

An array "package" may be the array plus only a substrate on which the array is deposited, although the package may include other features (such as a housing with a chamber).

A "chamber" references an enclosed volume (although a chamber may be accessible through one or more ports). It will also be appreciated that throughout the present application, that words such as "top," "upper," and "lower" are used in a relative sense only.

It will also be appreciated that throughout the present application, that words such as "cover", "base" "front", "back", "top", are used in a relative sense only. The word "above" used to describe the substrate and/or flow cell is meant with respect to the horizontal plane of the environment, e.g., the room, in which the substrate and/or flow cell is present, e.g., the ground or floor of such a room.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

DETAILED DESCRIPTION

Systems and methods for obtaining chemical array layouts are provided. The subject systems include a communications module and a processing module, where the processing module includes an array set developer configured to provide an array set decision in response to array request information received from a user and a layout developer configured to develop a chemical array layout based on an array set decision and information that includes array request information received from a user. A feature of embodiments of the subject systems is that the array layout developer includes a memory having a plurality of rules relating to array layout design, where the array layout developer is configured to develop an array layout based on the application of one or more of the rules to information that includes array request information received from a user. In certain embodiments, the processing module is further characterized by having at least one of the following additional features: (i) an array customizing manager configured to allow the array layout developer to develop an array that includes a first set of probe sequences provided by said user and a second set of probe sequences provided by an additional party; (ii) an array request information manager to provide a history of array request information to a user; (iii) an array layout format manager configured to provide an array layout format based on received array request information; (iv) an array layout customizing manager configured to receive a customer input array layout and suggest an alternative layout developed from information not provided by a user; (v) an array layout comparison manager configured to compare an array layout to a database of one or more array layouts; and (vi) a default probe set selection manager that allows said user to include or exclude a predetermined set of probes in said array layout. In certain embodiments, the methods further include a step of fabricating an array having features arranged according to an array layout determined by the system. In certain embodiments, the methods further include shipping such arrays, e.g., to a user of the system or third party. Also provided are computer program products for executing the subject methods.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, aspects of the invention include systems and methods of using the same which may be employed to produce array layouts for chemical arrays. In further describing the aspects of the invention, a review of representative system hardware/software architecture is provided, followed by a more detailed discussion of aspects of representative embodiments of the invention.

As summarized above, aspects of the invention include systems and methods for producing an array layout. Representative embodiments of the subject systems generally include the following components: (a) a communications module for facilitating information transfer between the system and one or more users, e.g., via a user computer, as described below; and (b) a processing module for performing one or more tasks in response to information received via the communications module of the system. In representative embodiments, the subject systems may be viewed as being the physical embodiment of a web portal, where the term "web portal" refers to a web site or service, e.g., as may be viewed in the form of a web page, that offers a broad array of resources and services to users via an electronic communication element, e.g., via the Internet. Each of these elements is described in greater detail below.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Sun Solaris, Linux, OS/400, Compaq Tru64 Unix, SGI IRIX, Siemens Reliant Unix, and others.

In certain embodiments, the subject devices include multiple computer platforms which may provide for certain benefits, e.g., lower costs of deployment, database switching, or changes to enterprise applications, and/or more effective firewalls. Other configurations, however, are possible. For example, so-called two-tier or N-tier architectures are possible rather than the three-tier server-side component architecture represented by, for example, E. Roman, Mastering Enterprise JavaBeans™ and the Java™2 Platform (John Wiley & Sons, Inc., NY, 1999) and J. Schneider and R. Arora, Using Enterprise Java. (Que Corporation, Indianapolis, 1997).

It will be understood that many hardware and associated software or firmware components that may be implemented in a server-side architecture for Internet commerce are known and need not be reviewed in detail here. Components to implement one or more firewalls to protect data and applications, uninterruptable power supplies, LAN switches, web-server routing software, and many other components are not shown. Similarly, a variety of computer components customarily included in server-class computing platforms, as well as other types of computers, will be understood to be included but are not shown. These components include, for example, processors, memory units, input/output devices, buses, and other components noted above with respect to a user computer. Those of ordinary skill in the art will readily appreciate how these and other conventional components may be implemented.

The functional elements of system may also be implemented in accordance with a variety of software facilitators and platforms (although it is not precluded that some or all of the functions of system may also be implemented in hardware or firmware). Among the various commercial products available for implementing e-commerce web portals are BEA WebLogic from BEA Systems, which is a so-called "middleware" application. This and other middleware applications are sometimes referred to as "application servers," but are not to be confused with application server hardware elements. The function of these middleware applications generally is to assist other software components (such as software for performing various functional elements) to share resources and coordinate activities. The goals include making it easier to write, maintain, and change the software components; to avoid data bottlenecks; and prevent or recover from system failures. Thus, these middleware applications may provide load-balancing, fail-over, and fault tolerance, all of which features will be appreciated by those of ordinary skill in the relevant art.

Other development products, such as the Java™2 platform from Sun Microsystems, Inc. may be employed in the system to provide suites of applications programming interfaces (API's) that, among other things, enhance the implementation of scalable and secure components. Various other software development approaches or architectures may be used to implement the functional elements of system and their interconnection, as will be appreciated by those of ordinary skill in the art.

In one embodiment, the system includes one or more Array Set objects and one or more Array Design objects. In one aspect, Array Design and Array Set objects comprise data elements corresponding to probe groups. In one aspect, Array Set and Array Design objects belong to their own domain and can be shared to other domains by a user with appropriate privileges. Array Set and/or Array Design objects may be organized hierarchically (e.g., as a set of versions, with a parent version being designed prior to a child version). In one aspect, the system comprises a difference engine for comparing different versions. Versioning allows users to make alterations to Array Sets and/or Array Designs while preserving completed work. Parent versions can have zero, one or more child versions where the child versions differ from each other in some fashion. Versions allow a user to select optimal features of one or more completed versions.

An Array Set and/or Array Design object may be associated with a plurality of attributes, such as, but not limited to, a unique database ID to uniquely identify the array set or array design, version number, name of the array set or array design, a description to further identify the set or design (e.g., type of array, such as an expression array, location analysis array, comparative genomic hybridization array), a product number associated with the set or design, status of the set or design (e.g., "in progress," "review," "complete," "draft," "locking," "submit"), a flag to identify whether the set or design version is the latest version, a flag to identify if the set or design is shared with other domains, keywords used to search a set or design, format identifier, status of available formats, e.g., provided by a vender user of the system (for example, obsolete, deprecated, active), link to an image file for a format, dimensions of a format, the URI to a template file for a format, a control reference associated with the set or design (e.g., identifying a set of control probes and their coordinates), a set of allowed controls (e.g., permissible numbers/locations/IDs of control probes) for a given format, the user ID of a person who created the set or design, creation date, last update date, the user ID of the person who last updated the set or design, domain reference, a set of probe groups for the set or design, parent array set or design, a set of one or more old versions of the set or design, domain shares (e.g., a set of domains to which this object has been shared to), numbers of features, size of features, orientation of features, coordinates of features comprising probes having particular probe IDs, numbers and locations of replicated features, numbers and/or locations and/or IDs of probes contributed by a particular user, numbers and/or locations and/or IDs of validated probes, numbers and/or locations and/or IDs of control/background probes, numbers of available features w/o probes, dimensions of interfeature areas, number of arrays on a substrate, density of features, and the like. As used herein, a "number" may also be provided as a percent, for example a number of probes may be represented as a percent of available features on an array template (e.g., on a virtual representation of an array).

As discussed above, Array Set objects and Array Design objects may include data elements relating to control probes as well as attributes associated with these controls (e.g., including, but not limited to, ID, status (e.g., obsolete vs. active), usage links, a flag to specify whether a control collection is randomized, location of probes, and the like.

The Array Set objects and Array Design objects may also include one or more data elements representing validation probes. In one aspect, a validation probe is associated with attribute(s) such as validation score, one or more probes identifiers corresponding to probes to which the validation probe has been compared, and the like. The system can also include a validation probe manager for creating/copying/updating/finding/deleting Validation Probe objects. In one aspect, a validation score is calculated by an algorithm that addresses target sequence data source, target sequence quality, base composition profiles, and heuristically validated rules. Computational methods and/or empirical methods can be used.

In one embodiment, the system comprises an Array Set object and/or Array Design object manager for creating/copying/updating/finding/deleting Array Set and/or Array Design objects. A user or users with requisite privileges will be allowed to create an Array Set and/or Array Design in the system. In one aspect, the manager includes a mechanism for computing dimension, probe composition, numbers and relative locations of features on a substrate or substrates (e.g., such as a glass wafer or slide). In another aspect, the system provides rules for computing positions of features based on the dimensions of a substrate or substrates selected by a user and optionally, other criteria. Such criteria may include a selected user cost for providing the array, experimental parameters, and the like. In one aspect, the system includes a knowledge base of array layouts that are associated with particular properties, which may include annotation categories. The knowledge base may be derived from empirical data, from predicted data (e.g., in silico modeling) or a combination thereof. For example, the knowledge base might include relationship(s) between a particular array layout design and hybridization of targets (e.g., nucleic acids, proteins) from one or more tissue types, fluorescence background, and the like. In certain aspects, the system can define array properties according to system rules, such as rules defining overall Tm of probes across the array, patterns of probes (e.g., such as control probes), numbers of replicated probes and their relative orientations.

In one embodiment, a user obtains an array layout (which may be an array set layout depending on the array set decision made by the system) by inputting a probe group selection using a user interface in communication with the system. In certain embodiments, the system operates by referring to a memory having a plurality of rules relating to array layout design, where the array layout developer function of the system is configured to develop an array layout based on the array set decision of the array set developer and application of one or more of the rules to information that includes array request information received from a user, as developed in greater detail below. The rules employed by the system may vary as desired, and might be empirically determined, learned by the system or derived using a combination of both approaches. In one aspect, the system randomizes the order of probes to be deposited or synthesized on a substrate or substrates (e.g., depending on the array set decision). The user may choose the dimensions and properties of the substrate(s) (e.g., material, shape, density, geometry of features, and the like) or the system may make one or more default selections relating to dimensions and properties for the user. The user may copy one or more properties of an array layout in certain embodiments, e.g., by requesting that the system display array designs stored in the system memory (and to which the user has privileges to access). Optionally, the system may display remarks associated with the designs such as empirically observed properties or predicted properties. In certain aspects, a user may search for an array layout by entering keywords relating to the properties. For example, a user may search for an array layout that has been, or might be used for, identifying genes expressed in a particular tissue type, species type, etc. Alternatively, or additionally, the user may search for probe groups that have been used for such a purpose, without regard to array layout and the system may optionally display array layouts associated with the probe groups in response to a further user request. A user may save an array layout as a version and modify a probe group used to create the array layout to include additional probes, delete probes, and/or modify probes. A user may use system-suggested control and/or validation probes and/or may add, delete or modify the probes. In one aspect, a user can direct the system to randomize probes on an in silico array layout or can impose a different order on the probes.

In certain aspects, a user may alter the order of probes on the array by pointing and clicking on features on a virtual representation of an array and moving the feature to different coordinates on the array. Similarly, a user may delete probes, copy probes, add probes and make other changes to the array layout by a point and click mechanism. Alternatively, a user can make such changes by altering coordinates of features of an array, and/or changing feature content (e.g., the sequence of a probe at a feature, the density of probes at a feature) by inputting such information into appropriate text fields on a user display, selecting check boxes, selecting one or more items from a drop-down menu, or by using a combination of such techniques.

In certain embodiments, the memory further stores a plurality of versions of an array layout. In these embodiments, at least two of the versions may be versions generated in response to input from a single user. In certain embodiments, at least two of the versions may be versions generated in response to input from at least two users. In certain embodiments, the processing module further includes a differencing engine for comparing the at least two versions. The output manager of such embodiments may communicate with an interface which displays differences between compared versions. In certain embodiments, the second version may be modified by a user to include or eliminate array layout characteristics of the first version. By array layout characteristic is meant an array layout parameter, such as feature content, format of features, etc. In certain embodiments, a new version of the array layout is generated which incorporates the modification.

In one aspect, the system automatically determines the appropriate center-to-center distance for a user-selected number of features on a user-selected substrate(s) of pre-defined dimensions (or may use a default substrate) or may select default center-to-center distances, inviting a user to fill in any open spaces on the array or to share such open spaces with other users who might want to share probe groups. In another aspect, if there are more probes than the dimensions of the array and the system-determined (and/or user-determined) distance between features allows, an alert may be provided to the user, e.g., in the form of an array set decision telling the user that an array set is required to array display all of the desired probes. However, in certain aspects, the system will randomly select excess probes and propose creation of a new array layout, e.g., that can be present on a single substrate. In certain other aspects, the system may select defined categories of excess probes, such as duplicate probes, control probes, and the like to eliminate from an array design to comply with a "make-it-fit" command. In still other aspects, the system may comply with such a command by altering a default or selected center-to-center distance between features on the array.

In certain embodiments, the system comprises a search engine for responding to user queries (e.g., inputted into a graphical user interface in communication with the system). In one aspect, each persistent object in the system memory has an associated table in a system database and object attributes are mapped to table columns. In a further aspect, each object has an object relational mapping file which binds that object to the table in the database. Objects are also associated with each other and this association is mapped as the relation between the tables. Objects are also associated with each other by many different relationships, such as one-to-one, one-to-many, many-to-one and many-to-many.

Search criteria may include descriptions of attributes or properties associated with an object and/or by values corresponding to those attributes. Relationships may also be used as search criteria. Basic search criteria can depend upon an object's attributes and advanced search criteria can depend upon association of the object with other objects, e.g., by searching properties of related objects.

In one embodiment, the search engine comprises a finder framework, which will construct a plurality of queryable conditions (e.g., all possible queryable conditions). When a user specifies an entity or object to search for, the framework generates all possible search conditions for that object and then gives the result as per the conditions selected by the user. A user of the system can search for probes, probe groups and/or array designs for different conditions. For example, a user can search for a probe that would fit into a certain annotation category. Search conditions may be different for different objects and in one aspect, a generic finder framework gives a generic solution for such searching. This feature is further described below.

In one aspect, after generating the conditions for searching, the finder framework localizes the names of attributes required for finding an object and displays the conditions to the user to specify the values for any number of conditions. Once the user specifies the search conditions with values, the framework executes the search and gets a collection of objects as result of search. In another aspect, the finder framework parses the mapping file of an object and all the other mapping files of its related objects to create simple and referential queryable conditions In certain embodiments, the search engine can build queries, save queries, modify queries, and/or update queries used to identify probes, probe groups, and/or array layout designs. In certain aspects, users with appropriate permissions can share, compare, modify and/or update queries. In certain other aspects, a user and/or the system can set the maximum output of a search and/or can rank search results according to fit to search criteria.

In response to a query, an output may be displayed by the system. For example, this output can include a list of values like Name, Creation Date, Status for the object, e.g., Array Set object or Array Design object, which are retrieved as search result. These values are properties of the object under search or its associated object(s). In one aspect, the result to be shown is displayed on a Webpage which includes capabilities for allowing possible actions. Such capabilities can include, but are not limited to, links, buttons, drop down menus, fields for receiving information from a user, and the like. In one aspect, for a probe group, such actions can include editing, comparing, etc. In certain aspects, the system further includes a result formatter for formatting search results (e.g., to build appropriate user interfaces such as Web pages, to specify links, provide a way to associate actions (e.g., "delete," "edit," etc.) with images, text, hyperlinks and/or other displays.

The system may also display the search criteria for an object under search on the web page. In one aspect, the system takes input data from the finder framework and creates a web page dynamically showing the search criteria for that object. In another aspect, the finder framework creates all possible queryable conditions for the object under search. These conditions are displayed on search web page as different fields. A user can select or specify value(s) for these field(s) and execute a search. The fields that are to be displayed have their labels in localized form. Fields may be in the form of a "select" box, or a text box or other area for inputting text. For example, a user may desire to search for a probe. A probe has queryable conditions that include, but are not limited to, probe name, sequence number (e.g., accession number), and the domain (e.g., a vendor domain).

In one embodiment, the search engine supports searching for different objects such as probe, probe group, and/or array layout design. In one aspect, the system provides a generic finder framework to create all queryable conditions for an object under search. Such conditions will generally depend upon the properties of the object and its relationship(s) with other objects. In another aspect, the finder framework retrieves localized field names for these conditions and their order and stores these in the system memory (e.g., in an objectdefinition.xml file). In one aspect, fields are displayed on a search page in the order in which they are stored in a file as a set of search parameters for which a user can select or enter values. The search parameters may be in the form of a list of objects and the parameters may relate to attribute categories. For example, in response to a user searching for a probe group, the system may display the queryable conditions: "name of probe group," "keywords used for search," "domain," "created by," "modified by," "modification date," "annotation" and the like. The finder framework can return the queryable conditions in the form of a collection, which can be displayed on a search page, which lists or represents the various search fields corresponding to the attribute categories in a localized form. A user may enter values for these fields and perform, e.g., selecting one or more of a probe having a specific name, providing specific keywords, identifying a desired domain, creator, modification date, annotation, and the like. The system then displays a list of probe groups that satisfy the search conditions. In one aspect, the system displays information regarding the criteria used to perform the search.

Search results can be shown on a web page, which may output a list of attributes associated with an object. For example, if a user is searching for Array Layout, the system may return a list of values like Name, Creation Date, Status of Array layout objects, etc.

The web page may be a reusable component, and can be used for showing related objects for an object under consideration, searching for them and adding/removing them according to the search criteria used for object under consideration. In some cases, objects are searched by the attribute values of other objects related to the object under search. For example, in case of an Array Set or Array Design search, a user can search Array Sets and/or Array Designs from the name of the Probe Group it contains. In certain aspects, a user is able to pick up the Probe Group names and add them to the search criteria of Array Design object or Array Set object. In one aspect, the system includes a "picker component" object for this selection purpose, which is a collection class for objects used for searching/associating an object with other objects.

In the above example, the following set of actions happen: first, the finder framework displays the search criteria for finding an Array Set and/or Array Design. Since Array Set and/or Array Design can be searched on the basis of Probe Group names, Probe Group name is one of the search criteria. It is a referential queryable condition for finding an Array Design. The finder framework will cause the system to display a link on the user interface, enabling a user to select a Probe Group and add its values for this referential queryable condition.

When user clicks on the link "SEARCH", the application initializes the picker component and since there are no Probe Groups selected for the referential queryable condition in the beginning, the collection of associated objects (Probe Group) in the picker component is empty. The system will then display a search page for Probe Group. A user is provided with the ability to search for different probe groups, e.g., by their attributes (such as name, creation date, annotation, and the like) and results are displayed. In one aspect, the page provides both a description of the search criteria as well as a search result.

Once a search for Probe Group is completed, a user can select Probe Groups and add them to a collection of associated objects to be displayed. A user can select or remove the Probe Group from this associated objects collection "Picker Components object." These associated objects are then added to the search criteria of Array Design or Array Set when the user presses a "Done" button.

In one aspect, the Picker Component object includes methods for taking attributes associated with an object as an input parameter and adding the object to a collection of associated objects (e.g., objects which have relationships with the input object). The Picker Component can also remove an object from a collection of associated objects. In one aspect, the Picker Component repeats the process of collecting associated objects and retrieves appropriate information from each object. In another aspect, the Picker Component arranges the information in a tabular form, which may be displayed on a Web page or reported in another suitable format.

In certain aspects, results of a search query may be linked to option fields allowing a user to order items associated with an object. For example, a checkbox may be included next to a probe group to allow a user to add the probe group to a shopping cart or directly order the probe group. Similarly, selecting an array design may cause the system to display options to purchase the array design. In certain aspects, the system may display items associated with objects that have relationships to objects associated with items being purchased. For example, if a user selects a Probe Group 1 for purchase, the system would display one or more array layouts that have included Probe Group 1 and/or reagents (e.g., such as controls, probes, labeling reagents, amplification reagents) that other users who have selected Probe Group 1 have purchased or which otherwise may be of interest to the user.

In one embodiment, a user enters into a session with the system. A session represents a series of requests from a particular user to a particular application of the system over a certain period of time. In one aspect, the system maintains a memory of a session object's state(s). The system may rely on this information in processing a new request.

In another embodiment, the system comprises a mechanism by which an administrator of the system can monitor the number of users connected to the system at a particular time. In one aspect, an administrator can invalidate the session of any user at any time, so that the user would not be able to access the system.

A variety of interfaces may be used to implement the functions of the system. In one embodiment, in the case of web applications, a servlet container uses an HTTP Session interface to create a session between an HTTP client and an HTTP server. The session may persist for a specified time period, across more than one connection or page request from a user. In one aspect, one user may be involved in a session, and the user may visit the web application many times. However, multiple users also may be involved in a session. The server can maintain a session in many ways, such as by using cookies or rewriting URLs.

In another embodiment, the system comprises a session manager. The session manager acts as a factory class that may be used to generate objects, and in one aspect, related objects when a user interacts with the system. In another embodiment, information relating to all user sessions is maintained in a collection within the session manager. In a further embodiment, one session manager instance is associated with one application in the system. In still a further embodiment, session instances are associated with session manager instances. This structure ensures that there are collections of instances per application in the system.

The session manager may have one or more of the following properties. The session manager may comprise a collection of all Session objects for all current users using the system or an application of the system. In one aspect, the collection is in the form of a Hashtable.

In one embodiment, the system contains a plurality of different application objects. Application objects comprise object representations of underlying database tables. In one aspect, each application has a context associated with it. Context is a logical area of the application, which contains the configuration information for the application. This information can be accessed within that application via this context.

For example, in one embodiment, the system comprises an application bootstrap framework, which comprises a set of classes and a configuration file. In one aspect, the configuration file contains configuration information for each application. The application bootstrapping mechanism starts working when the system starts up for the first time. When system starts up, a system initialization program (e.g., start up Servlet) instantiates an instance of Application object per application in the system. The first request to the application server will check whether application context for the named application is there or not. If application context is not present then it creates one. In one aspect, the application bootstrap framework communicates with an object/relationship mapping means in the system, assisting a user to identify object categories associated with a user query. In another aspect, in response to the identification of object categories, an output (e.g., such as a display on a graphical user interface) is generated In one embodiment, the system includes an event generation and processing framework. Whenever an action takes place on an object in the system, the system generates an event. The object that generates this event is called as the event source. In one aspect, when events occur, a user with requisite permissions is notified for these events. In certain aspects, to get an event notification, the user must register him/herself for that type of event. The user will get notifications only for those types of events for which the user has registered. For this, the system maintains a queue of the events, which contains only those events for which at least one user has registered. This queue is then processed periodically and notifications are sent to the users, e.g., by email. In one embodiment, the event notification framework generates events and adds them to the event queue, while the event processing framework processes the events from the event queue and then sends the notifications.

In one aspect, events supported by system application(s) are pre-configured. For example, the system memory can include a database of all supported (e.g., pre-configured events). In one aspect, the database includes a table comprising an event ID uniquely identifying a supported event (e.g., an annotation update), an action name for the event (e.g., "Annotation Update"), and name of an action that will be executed during post-processing of an event. The table may be a hashtable collection which may be associated with a particular user session by a session ID. In one aspect, the event manager allows a user to create, add and/or notify a user about events.

The Event Manager may include a mechanism for providing an output to a user which may include, but is not limited to the name of the event, an ID for an event uniquely identifying the event in the database, date of the event, content of an message to the user describing the event, type of event (e.g., triggered or periodic), and the like.

In certain aspects, a user may have an event manager associated with that particular user's events.

In a further aspect, the system comprises a Hashtable collection which contains a key-value pair of application name and session manager instance associated with an application. This collection is useful for identifying session manager instances for all applications in the system.

In one embodiment, a system according to the invention creates a session manager for an application if one did not already exist. In one aspect, the system may output data relating to all the session manager instances that are associated with the system (e.g., for all applications of the system). Similarly, the system may output information relating to the collection of session instances associated with any given session manager. The system may further remove a session from a session collection as well as invalidate a user session.

In one embodiment, the system further includes an instructional module that executes instructions from a computer program product for displaying Web pages that instruct a user how to use and interact with the system to order probe groups and/or arrays and/or associated reagents. In one aspect, the instructional module provides a tutorial page, explaining the purpose of the module (e.g., to provide instructions for designing and/or ordering arrays, and/optionally, defining terms (e.g., probe groups, arrays, array layouts, annotations). Additional Web pages or sections of web pages can be provided to describe and provide examples of various system functions (e.g., such as searching, uploading probes, downloading probes, etc.) and can provide interactive sessions to illustrate system functions. Such sessions can include displaying information relating to searching for information about probes, identifying probes, uploading probes, downloading probes, demonstrating sorting, viewing, saving search results, providing tutorials for generating an array layout, and the like. The instructional module can include a variety of graphics, including text, images, animation and can also provide accompanying voiceovers.

FIG. 4 provides a view of a representative system according to an embodiment of the subject invention. In FIG. 4, system 400 includes communications module 420 and processing module 430, where each module may be present on the same or different platforms, e.g., servers, as described above. The communications module includes the input manager 422 and output manager 424 functional elements.

Input manager 422 receives information, e.g., request information, from a user e.g., over the Internet. Input manager 422 processes and forwards this information to the processing module 430. These functions are performed using any convenient technique. Another of the functional elements of communications module 420 is output manager 424. Output manager 424 provides information assembled by processing module, e.g., array layout and/or probe related content, to a user, e.g., over the Internet, also in accordance with those known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources.

The communications module 420 may be operatively connected to a user computer 410, which provides a vehicle for a user to interact with the system 400. User computer 410, shown in FIG. 4, may be a computing device specially designed and configured to support and execute any of a multitude of different applications. Computer 410 also may be any of a variety of types of general-purpose computers such as a personal computer, network server, workstation, or other computer platform now or later developed. Computer 410 may include known components such as a processor, an operating system, a graphical user interface (GUI) controller, a system memory, memory storage devices, and input-output controllers. There are many possible configurations of the components of computer 410 and some components are not listed above, such as cache memory, a data backup unit, and many other devices. The processor may be a commercially available processor such as a Pentium® processor made by Intel Corporation, a SPARC® processor made by Sun Microsystems, or it may be one of other processors that are or will become available. The processor executes the operating system, which may be, for example, a Windows®-type operating system (such as Windows NT®4.0 with SP6a) from the Microsoft Corporation; a Unix® or Linux-type operating system available from many vendors; another or a future operating system; or some combination thereof. The operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

The input-output controllers of the computer could include any of a variety of known devices for accepting and processing information from a user, whether a human or a machine, whether local or remote. Such devices may include, for example, modem cards, network interface cards, sound cards, or other types of controllers for any of a variety of known input devices. Output controllers of input-output controllers could include controllers for any of a variety of known display devices for presenting information to a user, whether a human or a machine, whether local or remote. If one of the display devices provides visual information, this information typically may be logically and/or physically organized as an array of picture elements, sometimes referred to as pixels. A graphical user interface (GUI) controller may comprise any of a variety of known or future software programs for providing graphical input and output interfaces between the computer 410 and a user, and for processing user inputs. The functional elements of the computer 410 may communicate with each other via system bus. Some of these communications may be accomplished in alternative embodiments using network or other types of remote communications.

During use, a user employs the user computer to enter information into and retrieve information from the system. As shown in FIG. 4, computer 410 is coupled via network cable 415 to the system 400. Additional computers of other users in a local or wide-area network including an Intranet, the Internet, or any other network may also be coupled to system 400 via cable 415. It will be understood that cable 415 is merely representative of any type of network connectivity, which may involve cables, transmitters, relay stations, network servers, wireless communication devices, and many other components not shown suitable for the purpose. Via user computer 410, a user may operate a web browser served by a user-side Internet client to communicate via Internet with system 400. System 400 may similarly be in communication over Internet with other users and/or networks of users, as desired.

As reviewed above, the systems include various functional elements that carry out specific tasks on the platforms in response to information introduced into the system by one or more users. In FIG. 4, elements 432, 434 and 436 represent three different functional elements of processing module 430. While three different functional elements are shown, it is noted that the number of functional elements may be more or less, depending on the particular embodiment of the invention. Representative functional elements that may be carried out by the processing module are now reviewed in greater detail below.

In certain embodiments, the subject processing modules include at least one functional element that generates an array set decision based on information, e.g., array request information, received from one or more users, where this functional element is referred to herein as an array set developer. As defined above, an array set decision is a decision (i.e., determination) as to whether the total number of features required to array display a desired portion of the probe content of an array request information can be present in a single array format (such that it can be physically array displayed on a single array substrate surface) or exceeds an array format feature number limit such that an array set of two or more array formats is required for array display of the desired portion of the probe content of the array request information.

Depending on the format of the input array request information, which as reviewed above may vary, the array set developer may or may not proceed through one or more processing steps to identify the total number of features required to array display the desired portion of the probe content of the array request. With respect to desired portion, the desired portion may include the entire probe content (e.g., number of distinct probes) that is present in a given array request information. Alternatively, the desired portion may be some user defined and/or system defined subset of the total probe content of the array request information. For example, a user may specify that no redundant probes be present in the portion of the content of the array request information that the array set developer uses to identify the total number of different features, e.g., where the system may pick one of a plurality of different probes for the same target according to one or more appropriate rules. In certain embodiments where the array request information includes specific defined probes of specific sequence, the array set developer identifies the total number of probes by simply counting the total number of different probes in the array request information. In yet other embodiments where the array request information does not include specific sequences of desired probes, the array set developer may first determine specific probe sequences based on the content of the information and then total the number of determined probe sequences to arrive at the total number of features for the desired portion of the content of the array request information. In determining specific probe sequence from the array request information, the array set developer may include a probe design function sub-element or interact with a separate probe design functional element present in the system, such as the probe design functional element described in U.S. patent application Ser. No. 11/001,672 filed on Nov. 30, 2004, the disclosure of which is herein incorporated by reference.

In certain embodiments, identification of the total number of features required for array display of the desired portion of the probe content includes consideration of how different probe groups are to be array displayed. For example, the desired portion may include two or more different probe groups, where some of the groups are to be present on all arrays and other probe groups need only be present on a single array. For example, the probe content to be array displayed may include a first probe group that is a control probe groups, where the individual probes of this group are to be present on all of the different arrays (if multiple arrays are required). The probe content to be array displayed may also include a second probe group of experimental probes, which experimental probes need only be present on a single array. In these embodiments, in determining the total number of features required for array display of the probe content, if two or more array formats are required, the total number of probes in the control group(s) will be multiplied times the number of array formats in the array set and then added to the total number of probes in the experimental probe group(s).

Following identification of the total number of features required to array display the desired portion of the probe content of the input array request information, the array set developer then evaluates whether the identified total number of features exceeds a single array format feature number limit to determine whether a single array format or an array set of two or more array formats is required to array display the identified total number of features to provide an array set decision. As such, the array set developer compares the identified total number of features with a single array format feature number limit to determine if the total number of features can be physically produced on a surface of a single array substrate (in view of the desired array format parameters such as size and feature density) or must be physically produced on a surface of two or more array substrate surfaces because the total number of features exceeds the number of features that can be produced on a signal array substrate surface. For example, where the total number of features required to array display the desired portion of probe content is 35,000 and the maximum number of features that can be produced on a single surface of array substrate is 40,000, the array set decision provided by the array set developer is that a single array format is suitable for array display of the desired portion of the probe content of the array request information. Alternatively, where the total number of features required to array display the desired portion of probe content is 200,000 and the maximum number of features that can be produced on a single surface of array substrate is 40,000, the array set decision provided by the array set developer is that more than one, e.g., 5 different, array formats are required for array display of the desired portion of the probe content of the array request information.

The array set decision may then be employed by the array layout developer of the system, as reviewed below, or first provided to a user for review prior to forwarding to an array set developer. In those embodiments where the array set decision is first provided to a user for review, upon review the user may accept the array set decision and or request a modification, e.g., by requesting a change in one or more parameters employed by the developer in making the array set decision, such as the signal array format feature number limit, the total number of probe features, etc. This process may be iterative until the user accepts the array set decision, which accepted array set decision is then forwarded to the array layout develop for use in determining the array layout.

Aspects of the system further include an array a functional element that generates an array layout based on information received from one or more users, e.g., array request information, and an array set decision, e.g., as made by an array set developer as described above, where this functional element is referred to herein as an array layout developer. The array layout developer of the processing modules of the subject systems is a functional element that produces an array layout in response to receiving array request information and an array set decision. The array layout developer is configured to develop a chemical array layout in response to information received from one or more users, where the information received from the one or more users typically includes array request information, and the array set decision, e.g., as received from the array set developer of the system.

As reviewed above, by "array layout" is meant a collection of information, e.g., in the form of a file, that represents the location of probes that have been assigned to specific features of an array format or formats (e.g., where the array layout is an array set layout). As defined above, the phrase "array format" refers to a format that defines an array by feature number, feature size, cartesian coordinates of each feature, and distance that exists between features within a given array. As defined above, a subset of an array layout is an array set layout. By "array set layout" is meant a collection of information, e.g., in the form of a file, which represents the location of probes making up the collection of probe content of an array set that have been assigned to specific features of an array format of an array set. An array set layout is an array layout that encompasses an array set of two or more array formats. Array set layouts are array layouts that include two or more array formats and are present when an array set is required to array display the probe content of the desired portion of the array request information.

In certain embodiments, the processing module generates the array layout (which may be for a single array format or an array set layout made up of two or more array formats) by applying one or more rules, e.g., as embodied by Array Design Objects (described above) to the information provided by the user. As such, the processor may employ an object-oriented system, as described above, to apply one or more array design rules (e.g., rules about content, format, etc., as described above).

Aspects of the system include one or more rules on how to layout specific probes when an array set of two or more array formats is required to array display the total number of features, where the one or more rules are applied by the system in developing an array set layout. In certain embodiments, the rule that is applied by the system may be to randomly distribute individual probes (i.e., the desired probe content) among the different array formats of the array set to produce an array set layout. The probe content is considered to be randomly distributed if any single probe member of the content has an equal possibility of being present in any given array format of an array set. In yet other embodiments, a rule may be employed which includes a first type of probe group (e.g., control probe group) in each format of the array set (e.g., to provide a way of normalizing the signal intensities of each array in the array set) and then provides the remaining probes (e.g., of experimental probe group(s)) only in a single array format of the set, such that these remaining probes are not found in each array format of the array set. The system may apply different rules to different probe groups of the total number of probes, e.g., where control probes are provided in an array format according to specific placement rules, e.g., along the edge of the array, at predetermined varying intervals in an array format, etc., and the experimental probes are randomly distributed among the remaining feature locations of the array formats.

In certain embodiment, the experimental probe group(s) of the probe content of the array set may be distributed among the array formats of the array set according to some non-random rule or collection of rules. For example, probes corresponding to different chromosomal regions (e.g., as may be employed in a comparative genomic hybridization assay) may be distributed among the array formats according to chromosomal location, e.g., chromosome number of sub region thereof. For example, in a human nuclear genomic CGH experiment in which 5 different array formats are present in an array set, experimental probes that hybridize to locations of Chromosomes 1 to 5 may be present on the first array format of the set, experimental probes that hybridize to locations of Chromosomes 6 to 10 may be present on the second array format of the set, experimental probes that hybridize to locations of Chromosomes 11 to 15 may be present on the third array format of the set, experimental probes that hybridize to locations of Chromosomes 16 to 20 may be present on the fourth array format of the set, and experimental probes that hybridize to locations of Chromosomes 21, 22, X and Y may be present on the fifth array format of the set. Another example of where a non-random rule or collection of rules is employed to distribute experimental probes among array sets includes a gene expression analysis array set, in which probes whose expression pattern is associated with a particular phenotype of interest are present on a first array format and other probes are present on a second array format of the set.

A flow diagram of the interaction that occurs in certain embodiments between an array set developer and an array layout developer in producing an array layout in response to receipt of array request information is provided in FIG. 5. As can be seen in the embodiment shown in FIG. 5, a user inputs array request information in the system, as shown at step 520. The array set developer then identifies a total number of features required to array display the input array request information, as shown at step 530. Array set developer then makes an array set decisions, as represented by decision box 540, as to whether the total number of features exceeds an array format feature number maximum. If no, the array layout developer then produces an array layout for a single array format at step 560 and forwards the product array layout to user at step 570. If, at decision box 540, the array set decision is that the total number of features exceeds the array format feature number maximum, an array set decision is made at step 550 that an array set is required to array display the content of the array request information. At decision box 580, the user is given a choice as to whether to accept the array set decision. If yes, the decision is forwarded to the array layout developer which, at step 590, produces an array set layout. The product array set layout is then forwarded to the user at step 570. If the array set decision is not accepted at box 580, the user may modify the array request information at step 510, e.g., by reducing the content and/or increasing the maximum number of features, and this modified array request information is then input into the array set developer.

FIG. 6 provides a block diagram showing the interrelationships of different domains of a representative system according to an embodiment of the invention. As demonstrated, there is a many-to-many relationship between Probe Groups and Array Sets, were any given probe group can be found on one or more array sets, and any Array Set is comprised of one or more Probe Groups. There is a many to one relationship between Array Designs and Array Sets. With these relationships, the database structure allows one or more probe groups to be distributed across one or more Array Designs within an Array Set.

In certain embodiments, the processing module is configured to include an array-customizing manager. The array-customizing manager is a functional element that allows the array layout developer to develop an array which includes a first set of probe sequences provided by a user and a second set of probe sequences provided by an additional party, such as the system operator or a third party vendor. For example, if a given user has a set of known probes that the user wants to include in an array layout and ultimately an array having that layout, the user can introduce the desired set of probe sequences into the system. The array-customizing manager can then evaluate those uploaded sequences and suggest additional probes, e.g., in the form of an additional probe set or sets, each set having one or more probes, to include in an array layout. The array-customizing manager can display the additional probe set(s) to the user, and upon approval from the user, for the additional probe set(s) and user uploaded probe sequences to the array developer for production of an array layout. The array layout produced in these embodiments includes both user provided and third party provided, e.g., system operator or outside vendor, probe sequences. In this manner, the array-customizing manager is a functional element that allows the array layout developer to develop an array that includes a first set of probe sequences provided by a user and a second set of probe sequences provided by an additional party.

In certain embodiments, the processing module is configured to include an array request information manager. The array request information manager provides information to a user regarding the request information that was employed by the array layout developer in generating a given array layout. As such, the array request information manager provides a history of array request information to a user at the request of the user. The request information may be in the form of a compendium of queries, organized temporally or according to some other criterion, etc. As such, the customization manager provides a user the ability to retrace the steps employed in designing a given array layout, so that knowledge of the data that went into the development of the array layout can be readily obtained and used.

In certain embodiments, the processing module is configured to include an array layout format manager. The array layout format manager is a functional element configured to provide an array layout format based on received array request information. Specifically, the format manager will generate an array format in response to request information received from the user, where the manager may provide this array format to the user for acceptance or rejection. The array format manager can be configured to provide an array format that best uses resources, e.g., in terms of cost, based on the probes to be present in the array layout. Where the request information provided by the user is in the form of a complete layout and an initial format selection therefore, the array layout manager can evaluate the initial layout and suggest an alternative therefore, where the alternative may layout may provide one or more advantages with respect to the initial layout, e.g., in terms of price, etc. The format manager may also provide an array format that reduces or eliminates the number of redundant probes provided in an initial layout. In this manner, the array layout format manager is a functional element configured to provide an array layout format based on received array request information.

In certain embodiments, the processing module is configured to include an array layout customizing manager. The array layout customizing manager is a functional element configured to receive a user input array layout and suggest an alternative layout developed from information not provided by a user. For example, a user may input a given array layout (e.g., including an array set layout) and the layout customizing manager will then evaluate the input layout, where the evaluation will include consideration of information not used by the user in developing the initial layout. Such information may include updated annotation of one or more probes, costs for probes, additional probe sets available from third parties, and the like. The layout customizing manager may use this information to develop a new array layout, which layout is then provided to the user to for acceptance or rejection. In this manner, the array layout customizing manager suggests a new layout in response to receipt of an initial layout an evaluation of the layout with respect to information not considered by the user.

In certain embodiments, the processing module is configured to include an array layout comparison manager. The comparison manager is a functional element that is configured to compare a candidate array layout to a database of one or more array layouts. In comparing a given candidate layout to the database of one or more layouts, which may be catalog array layouts ready for immediate purchase or previously prepared array layouts from the same other users, the comparison manager may search for similar layout in the database, and offer that layout to the user instead of the candidate array layout submitted by the user. The offer may include a reduced fee for fabrication of the array, since it employs an array layout already in the database of the system. The comparison manager may also evaluate the candidate array layout to the collection of array layouts and identify, based on this comparison, additional probes that may be desirable to include in the candidate array layout. In certain embodiments, the original user that submitted or designed the chosen array layout may be notified that it is has been selected by another user. In this manner, the comparison manager is a functional element that is configured to compare a candidate array layout to a database of one or more array layouts.

In certain embodiments, the processing module is configured to include a default probe set selection manager. The default probe set selection manager is configured to allow a user to include or exclude a predetermined set of probes in a given array layout. For example, the system may include in a memory a probe set of probes that are always recommended to be in an array layout, at least with respect to a given type of array, where such probes may be employed as normalization probes, and the like. The default probe set selection manager may suggest the default probe set to the user for rejection or acceptance by the user. In certain embodiments, the default probe set selection manager evaluates the probes that have been placed on the array layout, evaluates the user's experimental goals (by menu selection) and makes recommendations based upon these evaluations. Evaluations includes, but are not limited to, probe characteristics (Tm, length, base composition, secondary structure, etc.), target characteristics (species, sequence quality, etc.) and empirical data (probe performance, expression profiles, etc.)

The above specifically described functions that may be performed by the array set developer and array layout developer are merely representative of different functions that may be performed by the array layout developer. In certain embodiments, the array layout developer performs two or more of the above specific functions, including three or more, four or more, five or more, as well as all of the above specific functions.

As summarized above, the systems of the invention receive array request information from a user and generate, based on the provided information and an array set decision, an array layout therefrom. The generated array layout is, in representative embodiments, forwarded to the user for evaluation and use. As such, the systems find use in at least generating array layouts. The array layouts generated by the subject systems can be layouts for any type of chemical array, where in representative embodiments the array layouts are layouts for biopolymeric arrays, such as nucleic acid and amino acid arrays. In representative embodiments, the layouts generated by the subject systems are for nucleic acid arrays.

In certain embodiments, the systems include probe design functionality, as described in copending application Ser. No. 11/001,672 filed on Nov. 30, 2004. In certain of these embodiments, the system includes a processing module configured to identify a probe sequence based on information regarding attributes of the plurality of data structures and then provide the identified probe sequence, or an identifier thereof, to a user.

In certain embodiments, the system is further configured to include a processing module with one or more of the following additional functionalities:

(i) a collaboration manager configured to allow at least two different users to jointly provide array request information to the array layout developer;

(ii) a security manager configured to control information transfer in a predetermined manner between at least two different users via said system; and (iii) a vendor manager configured to provide access by a user to a service provided by at least one vendor. Aspects of these additional functionalities have been reviewed above. Furthermore, these functionalities are reviewed in greater detail in copending application Ser. No. 11/000,681 filed on Nov. 30, 2004.

In certain embodiments, the output manager further provides a user with information regarding how to purchase an array or arrays according to the provided array layout. In certain embodiments, the information is provided in the form of an email. In certain embodiments, the information is provided in the form of web page content on a graphical user interface in communication with the output manager. In certain embodiments, the web page content provides a user with an option to select for purchase one or more synthesized arrays. In certain embodiments, the web page content includes fields for inputting customer information. In certain embodiments, the system can store the customer information in the memory. In certain embodiments, the customer information includes one or more purchase order numbers. In certain embodiments, the customer information includes one or more purchase order numbers and the system prompts a user to select a purchase order number prior to purchasing the one or more synthesized arrays.

In using the subject systems, as summarized above, a user or users input array request information into the system, e.g., via a user computer, as reviewed above. As reviewed above, the array request information may take a number of different forms, such as content information, format information, array layout review information, array layout approval information, etc. The system then takes the provided request information and ultimately generates a final array layout, e.g., by applying one or more array layout development rules to the array request information (as reviewed above). The final array layout is then forwarded to the user, e.g., via the user computer. In certain embodiments, the final array layout, and even request information used to generate the same, is stored on the system in a suitable memory element, where access to the stored information may be free to other users, or controlled in some way, as managed by a security manager, described above.

In certain embodiments, the user may choose to obtain an array having the generated array layout. Array fabrication according to an array layout can be accomplished in a number of different ways. With respect nucleic acid arrays in which the immobilized nucleic acids are covalently attached to the substrate surface, such arrays may be synthesized via in situ synthesis in which the nucleic acid ligand is grown on the surface of the substrate in a step-wise fashion and via deposition of the full ligand, e.g., in which a presynthesized nucleic acid/polypeptide, cDNA fragment, etc., onto the surface of the array.

Where the in situ synthesis approach is employed, conventional phosphoramidite synthesis protocols may be used. In phosphoramidite synthesis protocols, the 3'-hydroxyl group of an initial 5'-protected nucleoside is first covalently attached to the polymer support, e.g., a planar substrate surface. Synthesis of the nucleic acid then proceeds by deprotection of the 5'-hydroxyl group of the attached nucleoside, followed by coupling of an incoming nucleoside-3'-phosphoramidite to the deprotected 5' hydroxyl group (5'-OH). The resulting phosphite triester is finally oxidized to a phosphotriester to complete the internucleotide bond. The steps of deprotection, coupling and oxidation are repeated until a nucleic acid of the desired length and sequence is obtained. Optionally, a capping reaction may be used after the coupling and/or after the oxidation to inactivate the growing DNA chains that failed in the previous coupling step, thereby avoiding the synthesis of inaccurate sequences.

In the synthesis of nucleic acids on the surface of a substrate, reactive deoxynucleoside phosphoramidites are successively applied, in molecular amounts exceeding the molecular amounts of target hydroxyl groups of the substrate or growing oligonucleotide polymers, to specific cells of the high-density array, where they chemically bond to the target hydroxyl groups. Then, unreacted deoxynucleoside phosphoramidites from multiple cells of the high-density array are washed away, oxidation of the phosphite bonds joining the newly added deoxynucleosides to the growing oligonucleotide polymers to form phosphate bonds is carried out, and unreacted hydroxyl groups of the substrate or growing oligonucleotide polymers are chemically capped to prevent them from reacting with subsequently applied deoxynucleoside phosphoramidites. Optionally, the capping reaction may be done prior to oxidation.

With respect to actual array fabrication, in certain embodiments, the user may itself produce an array having the generated array layout. In yet other embodiments, the user may forward the array layout to a specialized array fabricator or vendor, which vendor will then fabricate the array according to the array layout.

In yet other embodiments, the system may be in communication with an array fabrication station, e.g., where the system operator is also an array vendor, such that the user may order an array directly through the system. In response to receiving an order from the user, the system will forward the array layout to a fabrication station, and the fabrication station will fabricate the array according to the forwarded array layout.

Arrays can be fabricated using drop deposition from pulsejets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. Other drop deposition methods can be used for fabrication, as previously described herein. Also, instead of drop deposition methods, light directed fabrication methods may be used, as are known in the art. Interfeature areas need not be present particularly when the arrays are made by light directed synthesis protocols.

A representative array fabrication device and system is depicted in FIG. 7. The apparatus shown includes a substrate station 120 on which can be mounted a substrate 10. Pins or similar means (not shown) can be provided on substrate station 120 by which to approximately align substrate 10 to a nominal position thereon (with alignment marks 18 on substrate 10 being used for more refined alignment). Substrate station 120 can include a vacuum chuck connected to a suitable vacuum source (not shown) to retain a substrate 10 without exerting too much pressure thereon, since substrate 10 is often made of glass. A flood station 168 is provided which can expose the entire surface of substrate 10, when positioned beneath station 168 as illustrated in broken lines in FIG. 7, to a fluid typically used in the in situ process, and to which all features must be exposed during each cycle (for example, oxidizer, deprotection agent, and wash buffer). In the case of deposition of a previously obtained polynucleotide (such as a polynucleotide fabricated by the iterative sequence used in forming polynucleotides from nucleoside reagents on a support, as described above), flood station 168 may not be present.

A dispensing head 210 is retained by a head retainer 208. The positioning system includes a carriage 162 connected to a first transporter 160 controlled by processor 140 through line 166, and a second transporter 100 controlled by processor 140 through line 106. Transporter 160 and carriage 162 are used to execute one axis positioning of station 120 (and hence mounted substrate 10) facing the dispensing head 210, by moving it in the direction of arrow 163, while transporter 100 is used to provide adjustment of the position of head retainer 208 (and hence head 210) in a direction of axis 204. In this manner, head 210 can be scanned line by line, by scanning along a line over substrate 10 in the direction of axis 204 using transporter 100, while line by line movement of substrate 10 in a direction of axis 163 is provided by transporter 160. Transporter 160 can also move substrate holder 120 to position substrate 10 beneath flood station 168 (as illustrated by the substrate 10 shown in broken lines in FIG. 7). Head 210 may also optionally be moved in a vertical direction 202, by another suitable transporter (not shown). It will be appreciated that other scanning configurations could be used. It will also be appreciated that both transporters 160 and 100, or either one of them, with suitable construction, could be used to perform the foregoing scanning of head 210 with respect to substrate 10. Thus, when the present application recites "positioning" one element (such as head 210) in relation to another element (such as one of the stations 120 or substrate 10) it will be understood that any required moving can be accomplished by moving either element or a combination of both of them. The head 210, the positioning system, and processor 140 together act as the deposition system of the apparatus. An encoder 130 communicates with processor 140 to provide data on the exact location of substrate station 120 (and hence substrate 10 if positioned correctly on substrate station 120), while encoder 134 provides data on the exact location of holder 208 (and hence head 210 if positioned correctly on holder 208). Any suitable encoder, such as an optical encoder, may be used which provides data on linear position.

Processor 140 also has access through a communication module 144 to a communication channel 180 to communicate with a distinct entity, e.g., a user or a system of the subject invention. Communication channel 180 may, for example, be a Wide Area Network ("WAN"), telephone network, satellite network, or any other suitable communication channel.

Head 210 may be of a type commonly used in an ink jet type of printer and may, for example, include five or more chambers (at least one for each of four nucleoside phosphoramidite monomers plus at least one for an activator solution) each communicating with a corresponding set of multiple drop dispensing orifices and multiple ejectors which are positioned in the chambers opposite respective orifices. Each ejector is in the form of an electrical resistor operating as a heating element under control of processor 140 (although piezoelectric elements could be used instead). Each orifice with its associated ejector and portion of the chamber, defines a corresponding pulse jet. It will be appreciated that head 210 could, for example, have more or less pulse jets as desired (for example, at least ten or at least one hundred pulse jets). Application of a single electric pulse to an ejector will cause a droplet to be dispensed from a corresponding orifice. Certain elements of the head 210 can be adapted from parts of a commercially available thermal inkjet print head device available from Hewlett-Packard Co. as part no. HP51645A. Alternatively, multiple heads could be used instead of a single head 210, each being similar in construction to head 210 and being provided with respective transporters under control of processor 140 for independent movement. In this alternate configuration, each head may dispense a corresponding biomonomer (for example, one of four nucleoside phosphoramidites) or an activator solution.

The amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The apparatus can deposit droplets to provide features which may have widths (that is, diameter, for a round spot) in the range from a minimum of about 10 µm to a maximum of about 1.0 cm. In embodiments where very small spot sizes or feature sizes are desired, material can be deposited according to the invention in small spots whose width is in the range about 1.0 µm to 1.0 mm, usually about 5.0 µm to 500 µm, and more usually about 10 µm to 200 µm.

The apparatus further includes a display 310, speaker 314, and operator input device 312. Operator input device 312 may, for example, be a keyboard, mouse, or the like. Processor 140 has access to a memory 141, and controls print head 210 (specifically, the activation of the ejectors therein), operation of the positioning system, operation of each jet in print head 210, and operation of display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the steps required by the fabrication station, or any hardware or software combination which will perform those or equivalent steps. The programming can be provided remotely to processor 141 through communication channel 180, or previously saved in a computer program product such as memory 141 or some other portable or fixed computer readable storage medium using any of those devices mentioned below in connection with memory 141. For example, a magnetic or optical disk 324a may carry the programming, and can be read by disk writer/reader 326. A cutter 152 is provided to cut substrate 10 into individual array units 15 each carrying a corresponding array 14b.

The operation of the fabrication station will now be described. It will be assumed that a substrate 10 on which arrays 14b are to be fabricated, is in position on station 120 and that processor 140 is programmed with the necessary array layout information to fabricate target arrays 14b (sometimes referenced as the "target array layout" or similar). Using information such as the foregoing array layout and the number and location of drop deposition units in head 210, processor 140 can then determine a reagent drop deposition pattern. Alternatively, the actual drop deposition pattern can be part of the array layout. In any event, the array layout can be provided to the fabrication station and communicated to memory 141 through communication channel 180. Processor 140 controls fabrication, in accordance with the deposition pattern, to generate the one or more arrays on substrate 10 by depositing for each target feature during each cycle, a reagent drop set. Further, processor 140 sends substrate 10 to flood station 168 for intervening or final steps as required, all in accordance with the conventional in situ polynucleotide array fabrication process described above. The substrate 10 is then sent to a cutter 152 wherein portions of substrate 10 carrying an individual array 14b are separated from the remainder of substrate 10, to provide multiple array units 15. The foregoing sequence can be repeated at the fabrication station as desired for multiple substrates 10 in turn. In a variation of the foregoing, it is possible that each unit 15 may be contained with a suitable housing. Such a housing may include a closed chamber accessible through one or more ports normally closed by septa, which carries the substrate 10.

Following array fabrication, the fabricated array may then be forwarded, i.e., shipped, to the user using any convenient means. As such, following fabrication, one or more array units may then be forwarded to one or more remote customer stations.

Chemical arrays produced according to array layouts generated by the subject systems and methods find use in a variety of different applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992. Also of interest are U.S. Pat. Nos. 6,656,740; 6,613,893; 6,599,693; 6,589,739; 6,587,579; 6,420,180; 6,387,636; 6,309,875; 6,232,072; 6,221,653; and 6,180,351. In certain embodiments, the subject methods include a step of transmitting data from at least one of the detecting and deriving steps, as described above, to a remote location.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

As such, in using an array made by the method of the present invention, the array will typically be exposed to a sample (for example, a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER available from Agilent Technologies, Palo Alto, Calif. Other suitable apparatus and methods are described in U.S. Pat. Nos. 5,091,652; 5,260,578; 5,296,700; 5,324,633; 5,585,639; 5,760,951; 5,763,870; 6,084,991; 6,222,664; 6,284,465; 6,371,370 6,320,196 and 6,355,934. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample or an organism from which a sample was obtained exhibits a particular condition). The results of the reading (processed or not) may be forwarded (such as by communication) to a remote location if desired, and received there for further use (such as further processing).

The invention also provides programming, e.g., in the form of computer program products, for use in practicing the methods. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture that includes a recording of the present programming/algorithms for carrying out the above described methodology.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A computer-based system for producing an array layout, said system comprising:
   (A) an input manager for receiving array request information from a user;
   (B) a processing module comprising a processor comprising:
      (i) an array set developer configured to:
         (a) identify a total number of features required to array display a selected portion of probe content of array request information; and
         (b) evaluate whether said identified total number of features exceeds a single array format feature number limit to determine whether a single array format or an array set of two or more array formats is required to array display said total number of features to provide an array set decision; and
      (ii) an array layout developer having a memory comprising a plurality of rules relating to array layout design, wherein said array layout developer is configured to develop an array set layout for an array set of two or more array formats based on application of one or more of a plurality of rules to information that includes array request information received from a user and said array set decision; and
   (C) an output manager for providing a first version of said array set layout to said user.

2. The system of claim 1, wherein said selected portion is the entire probe content of said array request information.

3. The system of claim 1, wherein said selected portion is less than the entire probe content of said array request information.

4. The system of claim 1, wherein said array set developer communicates said array set decision to said user for acceptance prior to providing said array set decision to said array layout developer.

5. The system according to claim 1, wherein a memory further stores a plurality of versions of said array set layout.

6. The system of claim 5, wherein at least two of the versions are generated in response to input from a single user.

7. The system of claim 6, wherein at least two of the versions are generated in response to input from at least two users.

8. The system of claim 6, wherein the processing module further comprises a differencing engine for comparing the at least two versions.

9. The system of claim 8, wherein the output manager communicates with an interface which displays differences between compared versions.

10. The system of claim 9, wherein a second version may be modified by a user to include a characteristic of the first version.

11. The system of claim 10, wherein a new version of the array layout is generated which incorporates the modification.

12. The system of claim 1, wherein said rules are modifiable by a permitted user of said system.

13. The system of claim 1, wherein said array set layout comprises organization of probe content on the array.

14. The system of claim 1, wherein the array format comprises system-defined layout parameters selected from the group consisting of numbers of features, density of features, dimensions of features, shape of features, size of interfeature areas, size of inter-array areas, and organization of probe content.

15. The system of claim 14, wherein the system-defined parameters include user-defined layout parameters.

16. The system of claim 1, further comprising one or more of the following:
   (i) an array customizing manager configured to allow said array layout developer to develop an array that includes a first set of probe sequences provided by a user and a second set of probe sequences provided by an additional party;
   (ii) an array request information manager to provide a history of said array request information to a user;
   (iii) an array layout format manager configured to provide an array layout format based on said array request information;
   (iv) an array layout customizing manager configured to receive a customer input array layout and suggest an alternative layout developed from information not provided by a user;
   (v) an array layout comparison manager configured to compare an array layout to a database of one or more array layouts; and (vi) a default probe set selection manager that allows a user to include or exclude a predetermined set of probes in said array layout.

17. A method of producing an array layout for a chemical array, said method comprising:
   receiving into a system according to claim 1, an array request information from a user; and
   obtaining an array layout from said system to produce said array layout.

18. The method according to claim 17, wherein said receiving is via the internet.

19. The method according to claim 18, wherein said receiving is via a graphical user interface.

20. A computer program product comprising a non-transitory computer readable storage medium having a computer program stored thereon, wherein said computer program, when loaded onto a computer, operates said computer to:
   (a) receive chemical array request information from a user;
   (b) develop an array set layout based on said received information and an array set decision by applying one or more array layout design rules to said received information and array set decision; and
   (c) provide said array set layout to a user.

* * * * *